United States Patent
Shinohara et al.

(10) Patent No.: US 7,705,167 B2
(45) Date of Patent: Apr. 27, 2010

(54) PROCESS FOR PURIFYING PROPYLENE OXIDE

(75) Inventors: Koji Shinohara, Ichihara (JP); Toshio Nakayama, Sodegaura (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 997 days.

(21) Appl. No.: 10/571,472

(22) PCT Filed: Sep. 15, 2004

(86) PCT No.: PCT/JP2004/013877

§ 371 (c)(1),
(2), (4) Date: Mar. 13, 2006

(87) PCT Pub. No.: WO2005/028461

PCT Pub. Date: Mar. 31, 2005

(65) Prior Publication Data

US 2007/0032671 A1    Feb. 8, 2007

(30) Foreign Application Priority Data

Sep. 18, 2003    (JP) ............................ 2003-325741

(51) Int. Cl.
*C07D 301/32*    (2006.01)
*C07D 301/19*    (2006.01)

(52) U.S. Cl. ..................................... 549/541; 549/529
(58) Field of Classification Search ................ 549/529, 549/541
See application file for complete search history.

(56) References Cited

U.S. PATENT DOCUMENTS

| 3,312,719 A | 4/1967 | Hullstrung |
| 3,607,669 A | 9/1971 | Jubin, Jr. |
| 3,843,488 A | 10/1974 | Schmidt et al. |
| 3,881,996 A | 5/1975 | Schmidt |
| 4,140,588 A | 2/1979 | Schmidt |
| 5,133,839 A | 7/1992 | Shih |
| 2005/0092593 A1 | 5/2005 | Oku et al. |

FOREIGN PATENT DOCUMENTS

| EP | 1 475 375 A1 | 11/2004 |
| JP | 50-7571 B1 | 3/1975 |
| JP | 50-83305 A | 7/1975 |
| JP | 54-30106 A | 3/1979 |
| JP | 2003-238547 A | 8/2003 |

OTHER PUBLICATIONS

E. Bartholome, et al., "Ullmanns Encyklopadie der technischen Chemie, 4. Aufl., Band 19", (1980) XP-002414225, pp. 471-472.

*Primary Examiner*—Bernard Dentz
(74) *Attorney, Agent, or Firm*—Sughrue Mion, PLLC

(57) ABSTRACT

A process for purifying propylene oxide, which comprises washing propylene oxide containing aldehydes and subsequently contacting an aqueous phase obtained with an extractant.

2 Claims, No Drawings

PROCESS FOR PURIFYING PROPYLENE OXIDE

TECHNICAL FIELD

The present invention relates to a process for purifying propylene oxide. More particularly, the present invention relates to a process for purifying propylene oxide, which efficiently separates aldehydes from propylene oxide containing the aldehydes.

BACKGROUND ART

As a producing process of propylene oxide, there is known a process in which an organic peroxide with propylene is reacted in the presence of an epoxidation catalyst.

In a liquid reaction mixture obtained by the reaction, water, hydrocarbons and oxygen-containing compounds such as methanol, formaldehyde, propionaldehyde, acetone and methyl formate, as impurities, are contained in addition to propylene oxide as a target product. Therefore, multi-stage purification steps become necessary to separate and recover propylene oxide of high purity from the liquid reaction mixture.

In purification of propylene oxide, it is publicly known to subject to extractive distillation using a hydrocarbon as an extractant. For example, U.S. Pat. No. 3,843,488 discloses that an alkane such as octane is effective for removing hydrocarbon impurities having 6 carbon atoms. Further, JP 50-007571 B discloses that an alkane such as octane is effective for removal of water. Furthermore, U.S. Pat. No. 5,133,839 discloses that a hydrocarbon such as octane is effective for removal of impurities such as methanol, propionaldehyde and acetone.

However, according to studies of the present inventors, in the above-described method, effective separation of aldehydes contained in propylene oxide was difficult.

DISCLOSURE OF THE INVENTION

An object of the present invention is to provide a process for purifying propylene oxide, which efficiently separates aldehydes as impurities contained in propylene oxide.

Namely, the present invention relates to a process for purifying propylene oxide, which comprises:

washing propylene oxide containing aldehydes with water; and subsequently contacting an aqueous phase obtained with an extractant.

BEST MODE FOR CARRYING OUT THE INVENTION

In the present invention, propylene oxide containing aldehydes is washed with water. The method of washing with water is not particularly restricted, it is usually carried out by mixing propylene oxide containing aldehydes with water, then separating into an oil phase and an aqueous phase. Herein, the aldehydes mean water-soluble aldehydes such as formaldehyde, acetaldehyde and propionaldehyde. Sufficient stirring is carried out in the mixing, subsequently, a phase separation into an oil phase and aqueous phase is carried out by leaving at rest or the like. As a mixing equipment for mixing propylene oxide containing aldehydes with water, commercially available common mixing equipments such as an agitator, a static mixer, a line mixer and an orifice can be used. When water soluble impurities such as alcohols (e.g. methanol, propylene glycol), water-soluble esters (e.g. methyl formate, methyl acetate) and organic acids (e.g. formic acid, acetic acid) in addition to the aldehydes, are contained, these are also dissolved in the aqueous phase. But, a part of propylene oxide is also simultaneously dissolved in the aqueous phase.

After the mixing, the mixture is subjected to phase separation into an aqueous phase and an oil phase by allowing to stand. As an oil-water separation equipment, though a common drum or a corelesser can be used, it is not particularly restricted if it is an equipment which can sufficiently leave at rest a mixture and separate into an oil and water. The number of washing may be one stage or multi stages. When the washing is conducted in multi stages, an aqueous phase in the latter stage may be recycled to an oil phase in the preceding stage. A mixing temperature is 5 to 100° C., and though an amount to be supplied of water can be properly determined taking account of contents of water-soluble impurities, the amount is usually 0.001 to 10 times the weight of propylene oxide to be supplied.

When the temperature is too high, loss of propylene oxide caused to thermal degradation becomes large, and when too low, performance of oil-water separation becomes inferior. Further, when water supplied is too small, removal efficiency of impurity decreases, and when too high, the amount of wastewater becomes larger and a wastewater treatment cost rises with the amount of wastewater, therefore, the above-described range is preferable.

Furthermore, it is effective for recovery of propylene oxide contained in water to supply water containing propylene oxide as water to be supplied.

After oil-water separation, most of propylene oxide exists in the oil phase and aldehydes transfer to the aqueous phase.

A part of propylene oxide in addition to the aldehydes is dissolved in the obtained aqueous phase. In the present invention, propylene oxide in the aqueous phase is selectively transferred to an extractant side, namely an oil phase side by contacting the aqueous phase with the extractant. The aldehydes in propylene oxide is separated thereby. A contact method is not especially restricted if it is a method in which propylene oxide transfers to the extractant side. As a preferable example, there is illustrated a method in which the aqueous phase and the extractant are mixed, and then the resulting mixture is separated into an aqueous phase and an oil phase. As a mixing equipment, the above-mentioned commercially available common mixing equipments such as an agitator, a static mixer, a line mixer or the like can be used. Further, as an oil-water separation equipment used after agitation, though a common drum or a corelesser can be used, it is not particularly restricted if it is an equipment which can sufficiently leave at rest and separate into an oil and water.

Furthermore, an operation for which a separated aqueous phase and an extractant are mixed and the mixture is subjected to oil-water separation, may be conducted.

The number of washing may be one stage or multi stages. When the washing is conducted in multi stages, an aqueous phase in the latter stage may be recycled to an oil phase in the preceding stage. A mixing temperature is 5 to 100° C., and an amount of the extractant to be supplied is usually 0.001 to 10 times the weight of propylene oxide contained in the aqueous phase.

When the temperature is too high, loss of propylene oxide caused to thermal degradation becomes large, and when too low, performance of oil-water separation becomes inferior. Further, when the extractant supplied is too small, efficiency for separating from the aqueous phase propylene oxide lowers, on the other hand, when too high, the cost rises due to increase of the amount of the extractant.

The used extractant excludes aliphatic hydrocarbons having 3 to 10 carbon atoms such as propylene, butane, pentane, hexane, heptane and octane, aromatic hydrocarbons such as ethylbenzene, cumene, toluene, xylene and benzene, wherein the hydrocarbons has a saturated water amount at 20° C. of 5000 ppm by weight or less.

Hydrocarbons having 3 to 10 carbon atoms are preferable since the saturated water amount is also small.

In the present invention, a raw material liquid to be subjected to separation may be propylene oxide containing aldehydes, for example, a reaction mixture after propylene oxide has been obtained by reacting an organic peroxide with propylene in the presence of a publicly known catalyst, which contains at least aldehydes as impurities, is preferably suitable. Further, the present invention can be also applied to propylene oxide containing hydrocarbons such as propylene, butane, pentane and hexane; water; alcohols such as methanol and propylene glycol; organic acids, ketones such as acetone; and esters such as methyl formate and methyl acetate in addition to aldehydes, obtained by reacting an organic hydroperoxide with propylene. However, in this case, it is preferable to use a liquid obtained after roughly separated by using a distillation column before washing with water because washing efficiency rises and losses of effective components such as propylene oxide and propylene can be reduced.

Moreover, in the present invention, purified propylene oxide can be obtained by, after propylene oxide contained in an aqueous phase has been transferred to a side of an extractant (oil phase), subjecting to said extractant to distillation. Furthermore, it is possible to effectively obtain purified propylene oxide by subjecting a mixture in which said extractant has been mixed with the above-described oil phase obtained by water washing, to distillation.

EXAMPLE

The present invention will be illustrated in detail referring to Examples below.

Example 1

An aqueous phase having the following composition was obtained by washing propylene oxide containing aldehydes with water at 20° C.:

Composition of aqueous phase

| Propylene oxide | 19% by weight |
| Acetaldehyde | 1.0% by weight |
| Methanol | 0.3% by weight |
| Formaldehyde | 0.1% by weight |

When, after 11 ton/hr of n-heptane as an extractant had been mixed to 1.9 ton/hr of the aqueous phase, oil-water separation was carried out with an orifice, contents of acetaldehyde and formaldehyde in an oil phase were less than 5 ppm and less than 10 ppm, respectively. Further, a content of propylene oxide in the oil phase was 3% by weight.

INDUSTRIAL APPLICABILITY

The present invention is a process for purifying propylene oxide, which comprises washing propylene oxide containing aldehydes with water and contacting an aqueous phase obtained with an extractant, and according to the invention, aldehydes can be effectively removed.

The invention claimed is:

1. A process for purifying propylene oxide, which comprises:
   washing propylene oxide containing aldehydes with water; and
   subsequently contacting an aqueous phase obtained with an extractant, wherein the extractant is a hydrocarbon having 3 to 10 carbon atoms.

2. The process according to claim 1, the process further comprising separating propylene oxide by distillation from the extractant obtained after contacting the aqueous phase with the extractant.

* * * * *